United States Patent [19]

Wolcott

[11] Patent Number: 4,460,448
[45] Date of Patent: Jul. 17, 1984

[54] CALIBRATION UNIT FOR GASES

[75] Inventor: Duane K. Wolcott, Baton Rouge, La.

[73] Assignee: The Dow Chemical Company, Midland, Mich.

[21] Appl. No.: 515,721

[22] Filed: Jul. 20, 1983

Related U.S. Application Data

[63] Continuation-in-part of Ser. No. 431,408, Sep. 30, 1982, abandoned.

[51] Int. Cl.³ .................. C25B 1/00; C25B 1/26; C25C 1/22
[52] U.S. Cl. .................................... 204/266; 204/98; 204/101; 204/265; 204/277; 204/278; 204/401
[58] Field of Search .............. 204/265, 266, 277, 278, 204/401, 481, 98, 101

[56] References Cited

U.S. PATENT DOCUMENTS

| | | | |
|---|---|---|---|
| 3,117,034 | 1/1964 | Tirrell | 204/265 |
| 3,458,414 | 7/1969 | Crane et al. | 204/149 |
| 3,761,376 | 9/1973 | Barstow et al. | 204/195 R |
| 3,761,377 | 9/1973 | Mang | 204/195 R |
| 3,764,269 | 10/1973 | Oldham et al. | 23/254 E |
| 3,966,413 | 6/1976 | Marinenko | 23/253 R |
| 3,969,209 | 7/1976 | Mueller | 204/195 R |
| 4,013,535 | 3/1977 | White | 204/252 |
| 4,035,255 | 7/1977 | Gritzner | 204/265 |
| 4,049,503 | 9/1977 | Becker | 204/1 T |
| 4,097,856 | 6/1978 | Yates | 204/237 |
| 4,118,194 | 10/1978 | Raleigh et al. | 422/98 |
| 4,172,015 | 10/1979 | Bamford et al. | 204/1 T |
| 4,179,347 | 12/1979 | Krause et al. | 204/149 |
| 4,191,618 | 3/1980 | Coker et al. | 204/98 |
| 4,235,690 | 11/1980 | Lichtgarn | 204/195 R |
| 4,250,126 | 2/1981 | Yates | 261/70 |
| 4,265,714 | 5/1981 | Nolan et al. | 204/1 T |
| 4,267,030 | 5/1981 | Brever et al. | 204/278 |
| 4,274,938 | 6/1981 | Schulten et al. | 204/266 |
| 4,312,720 | 1/1982 | Lefevre | 204/265 |
| 4,333,810 | 7/1982 | Wolcott et al. | 204/401 |
| 4,364,806 | 12/1982 | Rogers | 204/265 |

Primary Examiner—R. L. Andrews
Assistant Examiner—Terryence Chapman
Attorney, Agent, or Firm—A. J. Young

[57] ABSTRACT

This invention provides a calibration unit for generating known concentrations of an oxidizing or a reducing gas in an inert carrier gas. THe gas-generating electrode is sandwiched between an ion-exchange membrane and a porous diffusion membrane for minimizing the liquid layer thickness around the electrode and for regularizing the rate of diffusion of the gas generated. The present invention is especially useful for calibrating gas sensors which detect, measure, and monitor the concentration of a gas in the atmosphere, and for providing an accurate low concentration of gas for use wherever desired.

10 Claims, 1 Drawing Figure

CALIBRATION UNIT FOR GASES cl CROSS REFERENCE TO RELATED APPLICATIONS

This application is a continuation-in-part of an original application, Ser. No. 431,408, filed Sept. 30, 1982, now abandoned.

BACKGROUND OF THE INVENTION

This invention relates to a calibration device for producing a predetermined concentration of gases. More particularly, this invention relates to a portable electrochemical calibration unit for producing standard concentrations of oxidizing and reducing gases.

Two types of calibrators for the dynamic generation of low-level concentrations of gases in gas mixtures are widely used; i.e., permeation-tube calibrators and electrolytic calibrators. These calibrators are most often used to calibrate monitors for determining the safe or unsafe condition of a potentially hazardous gaseous environment, but may also be used to calibrate instruments for determining the concentration of any gaseous stream. For obvious reasons, the reliability and accuracy of calibrating these monitors and instruments is a very important function.

Permeation-tuybe calibrators utilize a sealed tube containing the gaseous material of interest. The tube is sealed with a polytetrafluoroethylene membrane, and the gas in the tube is maintained in the liquid state or in solution. Since polytetrafluoroethylene is permeable to a wide range of substances, molecules of the contained gas dissolve and diffuse through the membrane at a fixed rate into the surrounding atmosphere. If a diluent gas is passed around the permeation tube, precise and accurate concentration standards of specific gases can be generated by this method. The principal disadvantage of permeation-tube calibrators is their limited concentration selectively, limited portability and limited useful life.

In the electrolytic type of calibrator the pure gas is generated by passage of an electric current through a reagent electrolyte solution. The gas thus generated escapes as bubbles from the solution and is dispersed in a diluent gas stream to form a standard gas mixture of known concentration. As in the case of the permeation-tube calibrators, presently available electrolytic calibrators have the disadvantage of limited portability, as well as a lack of stability and sensitivity.

SUMMARY OF THE INVENTION

In general, the present invention provides an electrochemical calibration device for producing mixtures of known concentrations of the oxidizing or reducing gases in an inert carrier gas. An "inert carrier gas" as herein defined is any gas that will remain inert and not react with the oxidizing or reducing gases being generated under the conditions which exist when the calibration process is carried out.

An electrochemical cell is provided in the calibration device for generating oxidizing or reducing gases which includes a hollow body containing a first electrode and electrolyte, which electrolyte provides the ions that make up the oxidizing or reducing gases. The electrochemical cell also includes a second electrode at which the oxidizing or reducing gases are formed; an ion-exchange membrane which is disposed between and is in physical contact with the electrolyte and the second electrode thereby permitting transfer through the ion-exchange membrane of the ions forming the oxidizing or reducing gases from the electrolyte to the second electrode while substantially containing the electrolyte in the hollow body; a porous membrane in physical contact with and separating the second electrode from a mixing chamber outside the electrochemical cell through which the oxidizing or reducing gases defuse to the mixing chamber; and means for passing a known quantity of direct electrical current between the first and second electrodes to generate a known quantity of oxidizing or reducing gas at the second electrode. In addition to the electrochemical cell the calibration device includes means for passing a known quantity of inert carrier gas over the porous membrane in the mixing chamber to entrain the oxidizing or reducing gases in the inert carrier gas and generate a gaseous mixture having a known concentration.

It is an object of this invention to provide an electrochemical calibration unit for generating gaseous mixtures of known concentrations of oxidizing or reducing gases in an inert carrier gas. It is a further object of this invention to provide a calibration unit which is particularly suitable for portable field use. It is a still further object of the invention to provide a calibration unit which is rugged, accurate, dependable, and versatile. Other objects of the invention will be apparent to those skilled in the art from the more detailed description which follows.

DESCRIPTION OF THE PREFERRED EMBODIMENTS

Figure 1:
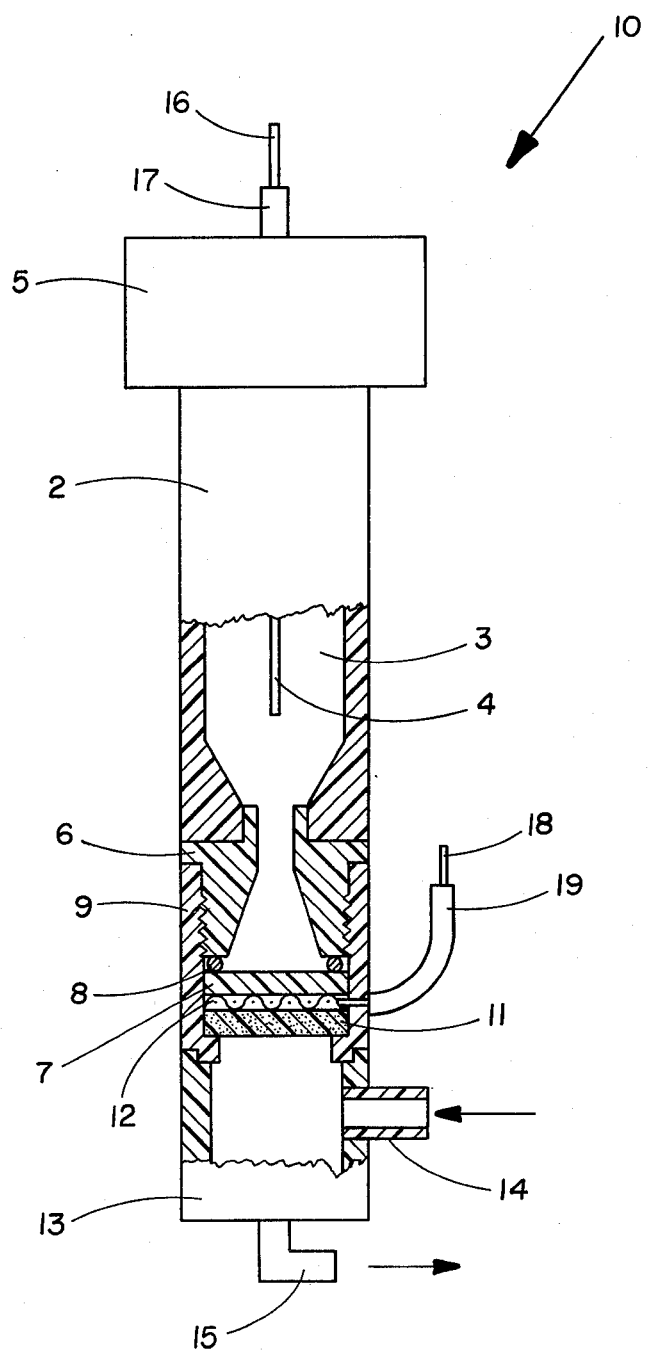
FIG. 1 is a partial cross-sectional view illustrating a calibration unit constructed according to the principles of the present invention.

The following description illustrates the manner in which the principles of the present invention are applied, but is not to be construed as in any sense limiting the scope of the invention.

More specifically, a calibration device 10 made according to the present invention is illustrated in FIG. 1. The calibration device 10 comprises a hollow cylindrical body 2 adapted to contain an electrolyte solution 3 in contact with a first electrode 4; means 5 for sealing the body 2 at the top thereof; means for sealing the body 2 at the bottom which include a threaded fitting 6, an ion-exchange membrane 7, and an O-ring 8; a nut 9 threaded onto the fitting 6; a porous membrane 11; a second electrode 12 formed of a metallic mesh disposed between and in physicl contact with the ion-exchange membrane 7 and the porous membrane 11; a flow-through mixing chamber 13; a first inlet tubing 14 to receive a stream of inert ccarrier gas; a second outlet tubing 15 to remove the stream of gas; a terminal connection 16 covered with electrical insulation 17 for the first electrode 4; and a terminal connection 18 covered with electrical insulation 19 for the second electrode 12. A direct electrical current source connected to terminals 16 and 18, and a means for supplying the stream of inert carrier gas to the inlet tubing 14 are not shown in FIG. 1, but are well known in the art.

The electrolyte solution 3 is generally a solution of an inorganic compound which, when electrolyzed, forms an oxidizing or reducing gas. For example, chlorine is beneficially generated by electrolyzing an aqueous solution of sodium chloride or hydrochloric acid. The first electrode 4 is preferably a platinum wire, and the second electrode 12 is preferably a substantially flat platinum-mesh or screen. The ion-exchange membrane 7 can be formed from any known ion-exchange membrane material, depending on the requirements of the calibration device 10. Preferably, if a cation-exchange membrane is desired, the membrane 7 is beneficially made from a material having a polytetrafluoroethylene backbone and perfluorinated two-carbon sulfonated sidechains, such as that marketed by E. I. du Pont de Nemours and Company, Inc., under the tradename "Nafion". If an anion-exchange membrane is desired, the membrane 7 is beneficially made from a styrene-divinylbenzene copolymer having quaternary-ammonium sidechains. The porous membrane 11 is prefereably fabricated from a polytetrafluoroethylene resin. The remaining structural elements of the device 10 can be constructed of any known structural material which will also provide electrical insulation for the electrochemical circuit. For example, a plastic material such as chlorinated polyvinylchloride may beneficially be used.

To complete the calibration device 10, a source of direct current is connected to the first and second electrodes 4 through 12 through the connections 16 and 18, respectively. The current may be measured by known means such as an ammeter, a microammeter, or a resistor in parallel combination with a voltmeter such as a ten-thousand ohm resistor in parallel with a Hickok LX-303 Digital Voltmeter. The source of direct current may be any well-known means such as a battery or an alternating power source which has been stepped down with a direct current transformer or rectifier, and may include feedback circuitry to insure current regulation when used in the calibration device 10. Although not absolutely required, a chart recorder may be used to provide a permanent record and the direct current measuring mean may be adapted to read out in the concentration of the gaseous mixture formed.

In general, a membrane is selected which will permit the transfer of the ion from which the oxidizing or reducing gas is generated. The choice of an ion-exchange membrane 7 depends upon the chemical species being generated by the device 10. If a halogen is to be generated, an anion-exchange membrane is chosen, to permit a flow of negative halide ions from the electrolyte 3 through the membrane 7 to the second electrode 12. If hydrogen is to be generated, a cation-exchange membrane is used, to permit a flow of positive hydronium ions from the electrolyte 3 through the membrane 7 to the second electrode 12. In addition, the membrane 7 substantially separates the electrolyte 3 from the second electrode 12, while permitting a small amount of solution to be carried with the ion of interest to the electrode 12, and also acts as a reverse ion barrier for ions which would poison the electrolyte 3 or electrode 4 is permitted to be transported into the cell.

Generally, The porous membrane 11 does not control the rate of release of the gas from the cell. Preferably, the average pore diameter of the porous membrane 11 is between about 50 microns and about 100 microns, and more preferably about 75 microns which is about one thousand times the molecular size of the most common gases of interest such as hydrogen and chlorine. However, as described in more detail hereinafter, it has been found that the porous membrane is a necessary element for the proper functioning of electrode 12. Although the porous membrane 11 is not rate-controlling, it does provide, to a minor degree, the added function of regularizing the rate of diffusion similar to many flow control devices such as surge chambers, thereby further smoothing the flow of the electrolytically-generated gas out of the thin film of liquid around electrode 12 into the stream of inert carrier gas.

As previously disclosed, the ion-exchange membrane 7, the second electrode 12, and the porous membrane 11 are in physical contact forming a sandwich structure. It has been found that this structure has a direct and substantial bearing on the accuracy and sensitivity of device 10. If the membranes 7 and 11 are not positioned close together a large layer of solution will form around the second electrode 12 during operation of device 10 in which gas bubbles will form and be released as erratic bursts. Moreover, the gas pressure build-up that occurs in a large layer of solution around the second electrode 12 during operation causes solution to be forced through the porous diffusion membrane 11 into the mixing chamber 13 which further decreases the sensitivity and accuracy of device 10. Thus, it has been found that the void volume not occupied by the second electrode 12 between the ion-exchange membrane 7 and the porous membrane 11 should be minimized to the point that gas bubbles will not form in and be released as erratic bursts from the liquid layer around the second electrode 12 during operation of device 10. In this regard, it has been found that a void volume of about ten microliters per square centimeter of the membranes 7 and 11 sandwiched together is the maximum volume which can be used without a substantial loss of accuracy and sensitivity in device 10. Of course, squeezing the membranes 7 and 11 closer together over the second electrode 12 will further decrease the void volume and increase the accuracy and sensitivity of the device 10. This void volume can, if physically possible, be reduced until there is only a molecular layer of solution around the second electrode 12 without detrimentally affecting the function of device 10.

A particularly preferred use of the calibration device 10 is for preparing standard gas samples containing trace concentrations of chlorine in air, as the inert carrier gas. For this purpose an anion-exchange membrane is required. The preferred material for forming the anion-exchange membrane is a styrenedivinylbenzene copolymer having quaternary-ammonium sidechains. The electrolyte solution 3 is preferably an aqueous solution of sodium chloride or hydrochloric acid. Upon passage of a current through the device 10, chlorine gas is generated at the second electrode 12 from a thin film of solution at the surface of the anion-exchange membrane 7. This type of electrolytic generation is inherently smooth and approaches theoretical output since it eliminates the need for large ballast volumes of electrolyte and chlorine gas, and high carrier gas flow rates which would be required if the chlorine were released in bursts or bubbles directly from the electrolyte. This improvement is achieved because of the use of the porous membrane 11 which minimizes the thickness of the liquid layer around electrode 12 sufficiently to prevent the formation of gas bubbles.

During use of device 10, air as the carrier gas flows into the chamber 13 through inlet 14 and across the surface of the membrane 11, where it entrains and mixes with the chlorine generated at the second electrode 12, thereby forming a mixture of chlorine and air. The direct current flowing through the electrodes 4 and 12 is accurately measured by known methods and the rate at which chlorine is generated is readily calculated from the known electrochemical stoichiometric equivalence.

The rate of air flow can be likewise accurately controlled and measured, for example, which an accurate gas pump and flowmeter. From the known rate of air flow and the known rate of chlorine generation, the concentration of chlorine in the air leaving the device 10 through the outlet 15 can be calculated with a high degree of accuracy, thereby providing a useful gas standard for calibrating other instruments or for use where very accurate known concentrations of a desired gas is required.

The present invention will now be further illustrated by means of the following examples.

EXAMPLE 1

The calibration device 10 was constructed with an anion-exchange membrane 11 made from a styrene-divinylbenzene copolymer with quaternary-ammonium sidechains to generate chlorine at a known, constant, and controlled rate from an electrolyte solution 3 consisting of a saturated aqueous solution of sodium chloride, while maintaining an air flow rate through the device 10 of one liter per minute. Current from a constant-current power source was passed through the electrolytic cell and measured with a microammeter. The data obtained are shown in Table I below.

TABLE I

| Current (microamperes) | Chlorine Concentration (parts per million by volume) | |
|---|---|---|
| | Theoretical | Actual-Produced |
| 33 | 0.23 | 0.20 |
| 69 | 0.48 | 0.50 |
| 88 | 0.61 | 0.60 |
| 191 | 1.32 | 1.35 |
| 344 | 2.37 | 2.35 |

While certain representative embodiments and details have been shown for the purpose of illustrating this invention, it will be apparent to those skilled in the art that various changes and modifications can be made therein without departing from the spirit and scope of the invention.

What is claimed is:

1. A calibration device for generating a gaseous mixture of known concentrations of oxidizing or reducing gases in an inert carrier gas comprising: an electrochemical cell for generating oxidizing and reducing gases, which includes a hollow body containing a first electrode and electrolyte, which electrolyte provides the ions that makeup the oxidizing or reducing gases; a second electrode at which the oxidizing or reducing gases are formed; an ion-exchange membrane which is disposed between and is in physical contact with the electrolyte and the second electrode, thereby permitting transfer of the ions forming the oxidizing or reducing gases through the ion-exchange membrane from the electrolyte to the second electrode while substantially containing the electrolyte in the hollow body; a porous membrane in physical contact with and separating the second electrode from a mixing chamber outside the electrochemical cell through which the oxidizing or reducing gases defuse into the mixing chamber; means for passing a known quantity of direct electrical current between the first and second electrodes to generate a known quantity of oxidizing or reducing gases; and means for passing a known quantity of inert carrier gas over the porous membrane in the mixing chamber to entrain the oxidizing or reducing gases in the inert carrier gas and generate a gaseous mixture having a known concentration.

2. The device of claim 1 wherein the void volume not occupied by the second electrode between the ion-exchange membrane and the porous membrane is minimized to the point that gas bubbles will not form in and be released as erratic bursts from the liquid layer that is formed in this void volume around the second electrode during operation of the device.

3. The device of claim 2 wherein the void volume has a maximum volume of about 10 microliters per square centimeter of the membranes.

4. The device of claim 3, wherein the porous membrane is formed from a polytetrafluoroethylene resin.

5. The device of claim 4, wherein the average pore diameter of the porous membrane is between about fifty microns and one-hundred microns.

6. The device of claim 5, wherein the average pore diameter of the porous membrane is about seventy-five microns.

7. The device of claim 1, wherein the ion-exchange membrane is an anion-exchange membrane.

8. The device of claim 7, wherein the anion-exchange membrane is formed from a styrene-divinylbenzene copolymer having quaternary-ammonium sidechains.

9. The device of claim 1, wherein the ion-exchange membrane is a cation-exchange membrane.

10. The device of claim 9, wherein the cation-exchange membrane is formed from a resin having a polytetrafluoroetylene backbone and perfluorinated two-carbon sulfonated sidechains.

* * * * *

UNITED STATES PATENT AND TRADEMARK OFFICE
CERTIFICATE OF CORRECTION

PATENT NO. : 4,460,448

DATED : Jul. 17, 1984

INVENTOR(S) : Duane K. Wolcott

It is certified that error appears in the above—identified patent and that said Letters Patent is hereby corrected as shown below:

Abstract, that portion of the abstract reading "THe" should read -- the --.

Column 1, line 1, "GASESc1 CROSS", should read -- GASES --; line 2, indent paragraph and insert -- CROSS --; line 26, "Permeation-tuybe", should read -- Permeation-tube --; line 38, "selectively,", should read -- selectivity, --.

Column 2, line 51, "physicl", should read -- physical --; line 54, "ccarrier", should read -- carrier --.

Column 3, line 14, "prefereably", should read -- preferably --; line 23, "through", should read -- and --; line 55, "is", should read -- if --; line 56, "The", should read -- the --.

Column 5, line 2, "which", should read -- with --.

Column 6, line 48, "polytetrafluoroetylene", should read -- polytetrafluoroethylene --.

𝔖igned and 𝔖ealed this

Twelfth Day of March 1985

[SEAL]

Attest:

DONALD J. QUIGG

Attesting Officer          Acting Commissioner of Patents and Trademarks